(12) United States Patent
Sarlikiotis et al.

(10) Patent No.: US 7,214,662 B2
(45) Date of Patent: May 8, 2007

(54) INJECTABLE SOLUTION OF AN LHRH ANTAGONIST

(75) Inventors: Werner Sarlikiotis, Peania (GR); Horst Bauer, Hersbruck (DE); Matthias Rischer, Frankfurt a. Main (DE); Jürgen Engel, Alzenau (DE); Frank Güthlein, Freiburg (DE); Dominique Di Stefano, Raunheim (DE)

(73) Assignee: Zentaris GmbH, Frankfurt (DE)

( * ) Notice: Subject to any disclaimer, the term of this patent is extended or adjusted under 35 U.S.C. 154(b) by 371 days.

(21) Appl. No.: 10/279,625

(22) Filed: Oct. 23, 2002

(65) Prior Publication Data

US 2003/0100509 A1   May 29, 2003

(51) Int. Cl.
*A61K 38/00* (2006.01)

(52) U.S. Cl. .................... 514/14; 514/12; 424/1.69

(58) Field of Classification Search .............. 514/14, 514/12; 424/1.69
See application file for complete search history.

(56) References Cited

U.S. PATENT DOCUMENTS

| 4,667,014 A * | 5/1987 | Nestor et al. ............. 530/313 |
| 5,140,009 A | 8/1992 | Haviv et al. |
| 5,300,492 A | 4/1994 | Haviv et al. |
| 2002/0039996 A1* | 4/2002 | Bauer et al. ............... 514/2 |
| 2004/0110689 A1* | 6/2004 | Garnick ..................... 514/16 |

FOREIGN PATENT DOCUMENTS

| EP | 0 299 402 B1 | 1/1989 |
| EP | 0 788 799 | 8/1997 |
| WO | WO 98/25642 | 6/1998 |
| WO | WO 00/47234 | 8/2000 |
| WO | WO 01/21194 | 3/2001 |
| WO | WO 01/82265 | * 11/2001 |
| WO | WO 01/87265 A2 | 11/2001 |

* cited by examiner

*Primary Examiner*—Cecilia J. Tsang
*Assistant Examiner*—Maury Audet
(74) *Attorney, Agent, or Firm*—Goodwin Procter LLP

(57) ABSTRACT

An aqueous injectable soution of an LHRH antagonist, such as Cetrorelix, in an organic, pharmaceutically acceptable acid, such as gluconic acid.

10 Claims, No Drawings

INJECTABLE SOLUTION OF AN LHRH ANTAGONIST

TECHNICAL FIELD

The invention relates to aqueous injection solutions of an LHRH antagonist with the use of additives of organic, physiologically tolerated acids and/or surfactants and their production for preventing the aggregation of LHRH antagonists in solutions. The injection solutions, prepared according to the invention, additionally lead to an increase in the bioavailability and enable the injection volume, which has to be applied, to be reduced.

STATE OF THE ART

For the controlled stimulation of the ovaries, followed by egg cell removal and techniques of assisted reproduction, aside from LHRH agonists (such as triptorelin, buserelin), especially LHRH antagonists (cetrorelix, ganirelix) have been used for some time, since they avoid the initial increase in endogenous gonadotropin secretion and lead immediately to a competitive inhibition of the gonadotropin-releasing hormone (EP 0788799 A2; EP 0299402 B1). The LHRH antagonist, ganirelix, is presently employed in a formulation, which contains 0.25 mg of ganirelix in 0.5 mL of an aqueous, mannitol-containing solution in the form of a ready-for-use injection (Orgalutran®). The LHRH antagonist cetrorelix (Cetrotide®) is presently offered in two forms, as a lyophilisate with 3 mg of cetrorelix, combined with a ready-for-use syringe, which contains 1 mL of water for reconstitution, and as a lyophilisate with 3 mg of cetrorelix, combined with a ready-for-use syringe, which contains 3 mL of water for reconstitution. However, LHRH antagonists are used not only for the controlled stimulation of the ovaries, but also for the treatment of the hormone-dependent types of cancer, such as prostate cancer. Substances such as abarelix (WO 98/25642) or cetrorelix (WO 00/47234) could be used for this purpose so that LHRH antagonists could be an alternative to the market-dominating agonists (leuprolide, goserelin) in this therapy. Because of the relative poor solubility of abarelix in water or physiological media, a sustained release formulation must be used, in order to achieve a prolonged effect. However, there are also indications that a prolonged effect may also require good solubility of the LHRH antagonists (G. Jiang, J. Stakewski, R. Galyean, J. Dykert, C. Schteingart, P. Broqua, A. Aebi, M. L. Aubert, G. Semple, P. Robson, K. Akinsanya, R. Haigh, P. Riviere, J. Trojnar, J. L. Junien and J. E. Rivier, J. Med. Chem., 2001, 44, 453–467).

PRESENTATION OF THE INVENTION

It is an object of the invention to prepare an injection solution, which has a low injection volume and an increased concentration of the LHRH antagonist due to the improved solubility of the latter. At the same time, the aggregation of the LHRH antagonist in the injection solution of greater concentration is prevented.

Surprisingly it was found that organic, physiologically tolerated acids, particularly carboxylic acids and especially hydroxycarboxylic acids, preferably, however, gluconic acid by itself or in combination with surfactants such as Tween, clearly improve the solubility of LHRH antagonists, and, with that, clearly reduce the tendency of these substances to aggregate.

The invention therefore enables LHRH antagonists to be produced in higher concentrations in aqueous solutions for injection. As LHRH antagonists, cetrorelix, teverelix, D-63153 (Ac-D-Nal-D-pCl-Phe-D-Pal-Ser-N-Me-Tyr-D Hci-Nle-Arg-Pro-D-Ala-$NH_2$), ganirelix, abarelix, antide and azaline B may, for example, be mentioned. It turned out that an excess of the respective carboxylic acid must be used and that equimolar amounts are not sufficient. Obviously, this effect cannot be explained alone by an in situ formation of salts with existing basic amino acids groups such as arginine, pyridyl alanine or lysine. Likewise, the surfactant concentration must not be too high as otherwise the solutions foam excessively and aggregation is induced once again by the surfactants.

At the same time, these additions make a higher bioavailability possible since they evidently also retard the spontaneous aggregation in the body after injection or make a more rapid absorption of the substance by the site of action possible. It turned out that the lower pH of such injection solutions (such as 2.5–3) does not have an effect on the local tolerance of the injection. By increasing the concentration, it is possible to reduce the volume applied, for example, in the case of the 3 mg form of cetrorelix, from 3 mL to 1 mL. It was also shown that a good shelf life can be achieved by these additions (see Example 1). When kept for more than 6 months at 24° C. and 60% R. H., there was, admittedly, an increase in contamination; however, in every case, the content was still clearly above 90% (usually the lowest value of the shelf life specification of pharmaceutical products). Cloudiness, as an indication of aggregation, increased only slightly. Cloudiness values of up to 8 FTU (formazin turbidity unit according to the European Pharmacopoeia) can readily be tolerated. Preservatives, such as phenol or p-chloro-m-cresol do not interfere and can be used additionally to preserve the solutions. The use of conventional structure-forming agents, such as mannitol, lactose, glucose and fructose is also possible.

DESCRIPTION OF ONE WAY OF CARRYING OUT THE INVENTION

EXAMPLE 1

| | |
|---|---|
| 500 mg | cetrorelix |
| 2 g | Tween 80 |
| 2.4 g | delta lactone of gluconic acid |
| 95 g | of mannitol | were mixed with water for injection purposes to form 2 L of a homogeneous solution. The solution was subsequently filtered to sterilize it and filled into ampoules. The ampoules were analyzed initially and after 6 months at 2°–8° C. and 25° C. at 60% relative humidity for purity (HPLC), content (HPLC), pH and aggregation (cloudiness).

Analytical Results:

| | Initial Analysis | Analysis after 6 months at 2°–8° C. | Analysis after 6 months at 25° C. and 60% R.H. |
|---|---|---|---|
| Purity (%) | 0.37 | 0.69 | 2.32 |
| Content (%) | 100.0 | 98.7 | 95.4 |

-continued

|  | Initial Analysis | Analysis after 6 months at 2°–8° C. | Analysis after 6 months at 25° C. and 60% R.H. |
|---|---|---|---|
| pH | 3.12 | 3.16 | 3.16 |
| Cloudiness (FTU) | 1.88 | 2.62 | 3.92 |

EXAMPLE 2 approx. 500 mg of D-63153
approx. 100 mg of Tween 60
approx. 475 mg of mannitol
were adjusted with aqueous, saturated gluconic acid delta lactone solution to a pH of about 2.5. A volume of about 50 mL resulted. It was stirred until a clear solution resulted.

Analytical Results:

Initially, the cloudiness of the solution was 2.4 FTU and, after 24 hours, it was 2.1 FTU. The purity profile and the content of the solution (HPLC) remained unchanged.

Structure of the LHRH antagonist D 63153:
Ac-D-Nal-pCl-D-Phe-D-Pal-Ser-N-Me-Tyr-D-Hci-Nle-Arg-Pro-D-Ala-NH$_2$

EXAMPLE 3 approx. 100 mg of teverelix
approx. 100 mg of Tween 80
approx. 475 mg of mannitol
were adjusted with aqueous, saturated gluconic acid solution to a pH of about 2.5. A volume of about 10 mL resulted. It was stirred until a clear solution resulted.

Analytical Results:

Initially, the cloudiness of the solution was 6.8 FTU and, after 24 hours, it was 8.4 FTU. The purity profile and the content of the solution (HPLC) remained unchanged.

Structure of the LHRH antagonist teverelix:
ac-D-nal-pCl-phe-3-D-pal-ser-tyr-D-H-cit-leu-ipr-lys-pro-D-ala-NH$_2$

We claim:

1. An aqueous solution of about 500 mg of one LHRH antagonist or a combination of LHRH antagonists selected from the group consisting of cetrorelix, teverelix, D-63153 (Ac-D-Nal-D-pCl-Phe-D-Pal-Ser-N-Me-Tyr-D-Hci-Nle-Arg-Pro-D-Ala-NH2), ganirelix, abarelix, antide, and azaline; about 2.4 g of an acid selected from the group consisting of carboxylic acid, hydroxycarboxylic acid, gluconic acid, and gluconic acid deltalactone; about 2.0 g Tween 80; about 95 g mannitol; in water; to form a solution with a volume of about 10 mL to 2 Liters.

2. An aqueous solution of about 500 mg D-63153; about 100 mg Tween 80; about 475 mg mannitol; in water; to form a solution with a volume of about 10 mL to 2 Liters.

3. An aqueous solution of about 100 mg teverelix; about 100 mg Tween 80; about 475 mg mannitol; in water; to form a solution with a volume of about 10 mL to 2 Liters.

4. The aqueous injectable solution of claim 1, wherein the acid is gluconic acid deltalactone.

5. The aqueous injectable solution of claim 1, wherein the LHRH antagonist is Cetrorelix and the acid is gluconic acid deltalactone.

6. The aqueous injectable solution of claim 1, wherein the volume of the aqueous injectable solution is about 10 mL.

7. A method for producing an aqueous injectable solution of an LHRH antagonist or a combination of LHRH antagonists, as in any of claims 1–3, 4–5, or 6, which comprises either (a) compounding an injectable solution of an LHRH antagonist; Tween; and mannitol in a pharmaceutically acceptable organic acid and water; or (b) dissolving an LHRH antagonist; Tween; and mannitol in a pharmaceutically acceptable organic acid; homogenizing the resulting solution; and recovering it in an injectable form.

8. The method of claim 7, wherein said acid is a carboxylic acid.

9. The method of claim 8, wherein said acid is hydroxycarboxylie acid.

10. The method of claim 9, wherein said acid is gluconic acid deltalactone.

* * * * *